United States Patent [19]
Bent et al.

[11] 3,984,570
[45] Oct. 5, 1976

[54] PROCESS FOR COMBATING FUNGI

[75] Inventors: Keith Joseph Bent, Crowthorne; John Angus William Turner, Wokingham, both of England

[73] Assignee: Imperial Chemical Industries Limited, London, England

[22] Filed: Feb. 11, 1974

[21] Appl. No.: 441,390

[30] Foreign Application Priority Data
Feb. 22, 1973  United Kingdom.................. 8753/73
July 6, 1973   United Kingdom................ 32213/73

[52] U.S. Cl................................. 424/341; 424/303; 424/315; 424/312; 424/317; 424/318; 424/325; 424/329
[51] Int. Cl.²........................................... A01N 9/24
[58] Field of Search..................... 424/341

[56] References Cited
UNITED STATES PATENTS
3,833,736   9/1974   Frick et al. .......................... 424/343

OTHER PUBLICATIONS
Chemical Abstracts 61:16715e (1964).
Chemical Abstracts 70:67048k (1969).

*Primary Examiner*—Leonard Schenkman
*Attorney, Agent, or Firm*—Cushman, Darby & Cushman

[57] ABSTRACT

Compositions containing certain surface active agents are used to combat overwintering fungal diseases in plants. Particularly perferred surface active agents are condensates of alkyl phenols or straight or branched chain fatty alcohols with from 3 to 50 moles of ethylene oxide.

4 Claims, No Drawings

PROCESS FOR COMBATING FUNGI

This invention relates to a process for combating fungi. More particularly it relates to a process for combating overwintering fungal disease, for example the mycelium and spores of fungi harboured by trees during their winter dormancy period and giving rise to actively-spreading fungal disease when the tree resumes active growth in the following spring and summer.

It has been known for some years, for example, that the successful perennation of the apple mildew fungus, *Podosphaera leucotricha*, is due to its ability to survive the winter in vegetative and fruiting buds. In the spring and early summer these buds give rise to diseased tissues (primary infections) and thereafter the disease spreads during the growing season. It therefore follows that the occurrences of the disease in summer would be reduced if a means for combating the overwintering disease located in the buds were established.

Attempts have been made in the past to establish a process for effectively combating overwintering mildews (fungi) but no treatment so far proposed has achieved any positive degree of commercial usage or success, or even general approval. Thus the treatment of overwintering infected buds and apple rootstocks of apple trees using dinitro-ortho-cresol (DNOC) emulsified in petroleum-oil was attempted, with little success, in the years 1954 to 1961. Results are reviewed in an article by Moore, Bennett and Burchill entitled "Further Studies of the influence of oil-emulsion sprays on bud infections of apple mildew". (Report of the East Malling Research Station for 1961, pages 97 to 100). Since that time little further work appears to have been done on investigating methods for combating overwintering mildew.

In so far as conventional mildew control methods are concerned, that is the spraying of actively-growing vegetation, it is known that certain surface active agents are anti-fungal in their own right when sprayed onto the foliage of actively growing plants. Thus in the Canadian Journal of Botany 42, (1964), page 1335 there appears an article by F. R. Forsyth entitled "Surfactants as fungicides" which shows that surface active agents are fungistatic. Again in Annals of Applied Biology (1963), 52, pages 45 to 54 appears an article entitled "Greenhouse Evaluation of Chemicals for the Control of Powdery Mildews" by Kirby and Frick, similarly pointing out the achievement of fungal disease control using substances having surface active properties. These are but two of many references showing that surface active agents per se are fungicidal. In addition, the literature on the subject of mildew control includes many references to the use of fungicidal substances well known in the art, either alone, or in conjunction with surface active agents for this purpose. None of these treatments, however, has been successfully applied to combat overwintering mildew, and no doubt failure of the overwintering DNOC/oil treatments referred to above must have played some part in dissuading researchers from attempting to apply established mildew-active materials to overwintering mildew situations. Indeed the small amount of recent research published has pointed away from there being considered any value in the latter approach. Thus it has recently been shown by E.L. Frick and R.T. Burchill (Plant Disease Reporter Volume 56, No. 9 September 1972) that substantial eradication of apple powdery mildew from infected buds of apple trees was obtained with applications in the dormant season of mixtures of methyl esters of fatty acids or mixtures of fatty alcohols. Substantially normal shoot growth occurred in the following spring. The aforesaid mixtures of esters or alcohols were known to act as so-called "chemical pruning agents", more especially as sucker growth inhibitors in tobacco plants and ornamentals either alone, or in conjunction with other chemicals, as reported in U.S. Pat. Nos. 3,340,040; 3,326,664; and 3,438,765 and hence were known bud penetrants.

It has now been found, surprisingly, that other chemical substances may be used to combat overwintering mildews (fungal diseases) and that the use of these substances has the advantages that it involves less risk of undesirable damage (phytotoxic effects) occurring in the treated trees. For example they are less likely to kill off healthy buds.

By the term "tree" in this specification is intended any plant, cane, vine, shrub, bush, tree or other vegetation which is ornamental or produces an edible crop, ornamental blooms, or useful substances. Examples of crop-producing trees are fruit trees, such as apple, peach and pear trees. Examples of ornamental plants are roses. Examples of useful-substance producing trees are rubber trees.

Accordingly the present invention provides a process for combating overwintering fungal disease comprising applying to ornamental, edible fruit producing, or useful substance producing, plants, bushes, shrubs or trees, whilst in, or approaching, a dormant phase, an effective anti-fungal amount of a composition comprising a substance having surface active properties.

The advantage of overwintering treatments, for example the treatment of apple trees to combat apple powdery mildew when the trees are dormant, or near dormant, is that if a substantial reduction of the mildew inoculum (e.g. spores and mycelium) can be secured, then the amount available to spread the disease in the following spring is diminished, and since the incidence of disease is lessened this in turn allows a reduction in the frequency or dosage of conventional fungicide treatments actually made in the spring and summer. There is also a diminishment of the need for removal of diseased tissues by mechanical excision, or pruning, which are time-consuming and costly operations. Although, as has been previously mentioned, surface active agents are per se fungicidal, they are used in practice as adjuvants for chemical substances of proven fungicidal efficacy rather than as fungicides themselves. Reasons for this include the fact that used alone they tend to produce either an unacceptable degree of phytotoxic damage to actively-growing trees or unacceptably low degrees of mildew control. In the situation in which the plant or tree is in, or approaching, a dormant phase, however, it has been found, surprisingly, that higher rates of surface active agents can be applied without causing unacceptable damage to the tree, especially the buds thereof, and at the same time producing a mildew-combating effect.

The invention process combats, in particular, overwintering powdery mildew diseases and, for example, is effective against *Podosphaera leucotricha* in apple tree buds.

In one preferred aspect, therefore, the invention provides a process for combating the overwintering disease *Podosphaera leucotricha* in apple trees which comprises spraying the trees whilst in, or approaching, a dormant phase with an effective amount of an aqueous solution, dispersion or emulsion containing at least 0.5% by volume of a substance having surface active properties.

The invention process, however, may also be used to combat other overwintering fungal diseases such as, for example, downy mildew diseases, Dibotryon, Fabraea, Taphrina, Nectria cankers, and Rust diseases. These diseases may occur on, for example, trees, shrubs, vines or canes.

Particular examples of particular trees and shrubs, and fungal diseases which affect them which may be combated by the invention process are as follows:

| "Tree" | Disease |
| --- | --- |
| Apple | Podosphaera leucotricha |
| Pear | Podosphaera leucotricha |
| Peaches | Taphrina deformans |
| Vine | Plasmopara viticola |
| Rubber | Oidium heveae |
| Roses | Sphaerotheca pannosa |
| Vine | Uncinula necator |

The treatment may be effected in a variety of ways. Preferably the tree is sprayed with a liquid containing a substance having surface active properties, but dusting with a powdered formulation containing or consisting of a substance having surface active properties may also be employed, as may the application of foams containing a substance having surface active properties.

The treatment of the tree is effected whilst the tree is in a dormant phase, or when it is approaching a state of dormancy, that is when active growth has ceased and the leaves have either fallen off the tree or are about to fall off. Preferably, therefore, treatment is effected in the Autumn, or during Winter, but it may also be carried out nearer the Spring, and even up to the stage just before the buds commence to burst. Within these stages of approaching dormancy and actual dormancy any number of treatments may be carried out. The occasion, and number of, treatments may therefore be varied for optimum effect depending upon the type of tree and species of fungus being combated.

The concentration of the substance or mixture of substances having surface active properties in the composition used to treat the tree may vary within wide limits and will depend upon a number of factors including the need to obtain a useful effect and the obvious requirement of mitigating harmful effects, that is phytotoxic effects, which might result, in an extreme case, in damage to, or death of, the buds for example. A further factor is the rate of application, that is the actual volume of composition applied. Thus if high volumes are used a lower concentration of substance having surface active properties may be present in the composition used for treatment, whilst if low volumes are applied a higher concentration of the surface active substance can be present in the composition. In general at least 0.5% by volume of the substance having surface active properties should be present in the composition, the remainder of which is constituted by a solid or liquid carrier. In an extreme case the substance having surface active properties may be used per se, that is without dilution, but, by way of example only, the composition may contain, as an upper limit, from about 10% to 20% by volume of the substance having surface active properties. Preferred compositions contain about 5% by volume of surface active agent and are sprayed onto trees in sufficient amount to wet the branches and tree generally. Water is a preferred liquid diluent. It may be used alone or admixed with an amount of an alcohol containing from 1 to 4 carbon atoms.

When the composition is a liquid, as is preferred, and this is applied by spraying, a wide variety of spraying techniques may be employed including the use of simple knapsack sprayers with nozzles and jets, and the use of motor-driven sprayers which are hydraulically operated or air-assisted, e.g. to blow a mist, and these may be carried by an operator or be mounted on wheels and, if desired, be self-propelled or towed. Aerial spraying techniques may also be used. Thus the tree may be sprayed from above and below the branches, or at branch level, or at a combination of levels and spray booms fitted with a plurality of spray nozzles may be employed for this purpose. Preferably the entire tree is treated but, if desired, selected branches only may be treated. As an alternative to spraying, a liquid composition comprising a substance having surface active properties, may be applied in the form of a foam. Such methods of foam-application are advantageous in that they achieve a high application rate since the foam adheres to the branches of the tree.

The surface active agent, that is the substance having surface active properties, may be cationic, anionic, or non-ionic in character; or it may be a mixtrue of one or more surface active agents. If such a mixture is used it will normally comprise either an anionic or cationic agent in admixture with a non-ionic agent, or a mixture of two, different non-ionic agents, but "amphoteric" surface active agents, that is compounds of mixed anionic-cationic structure may be used. Suitable agents of the cationic type include, for example, long chain amine condensates with ethylene oxide, quaternary ammonium compounds, for example, cetyltrimethyl ammonium bromide. Suitable agents of the anionic type include for example soaps, for example hard, soft and amine soaps, salts or aliphatic monoesters of sulphuric acid, for example sodium lauryl sulphate, salts of sulphonated aromatic compounds, for example sodium dodecylbenesulphonate, butyl-naphthalene sulphonate, a mixture of the sodium salts of diisopropyl — and triisopropyl-naphthalene sulphonic acids, and sodium salts of N-alkylated-N-fatty acid taurats and isethionates, and sodium salts of long chain sulphonated dicarboxylic acids. Suitable agents of the non-ionic type include, for example, the condensation products of ethylene oxide with fatty alcohols such as oleyl alcohol or ceryl alcohol, or with alkyl phenols such as octylphenol, nonylphenol, and octylcresol. Other non-ionic agents are the partial esters derived from long chain fatty acids and the condensation products of the said partial esters with ethylene oxide, the lecithins, and polyoxyethylene ethers of mixed partial fatty acid esters of sorbitol anhydrides.

Suitable specific surface active agents which may be used in the invention process are set out below in Table I. In the left hand column there is given the Trade Mark by which the product is known whilst in the right hand column is presented as accurate as indication as is possible of its chemical constitution. The exact chemical nature and make-up of some of the surface active agents mentioned is not known.

TABLE I

| No. | Trade Mark | Chemical Constitution |
|---|---|---|
| 1 | "AGRAL" 90 | Is a mixture of 90% Lissapol NX (see below) and 10% methylated spirit (methanol). |
| 2 | "AEROSOL" OT 75 | Is a 75% solution of sodium dioctylsulphosuccinate in alcohol/water. The alcohol is believed to be isopropanol. |
| 3 | "TWEEN" 20 | Polyoxyethylene Sorbitan monododecanoate. |
| 4 | "TWEEN" 80 | Polyoxyethylene Sorbitan mono (1-octadecanoate). |
| 5 | DDAB | Didecyldimethylammonium bromide. |
| 6 | "LUBROL" L | A condensate of 1 mole of nonyl phenol with 13 molar proportions of ethylene oxide. |
| 7 | "LUBROL" APN 5 | A condensate of 1 mole of nonyl phenol with 5½ moles of ethylene oxide. |
| 8 | "LISSAPOL" NX | A condensate of 1 mole of nonyl phenol with 8 moles of ethylene oxide. |
| 9 | "RENEX" 30 | A branched chain tridecyl alcohol with 12 moles of ethylene oxide. |
| 10 | "LUBROL" W | A condensate of a mixture of $C_{16}$ to $C_{18}$ alcohols with 17 moles of ethylene oxide. |
| 11 | "BRIJ" 35 | A condensate of dodecyl alcohol with 23 moles of ethylene oxide. |
| 12 | "ETHYLAN" D259 | A condensate of $C_{12}$ to $C_{15}$ alcohol alcohols with 9 moles of ethylene oxide. |
| 13 | "TRITON" X100 | A condensate of 1 mole of octyl phenol with 9 to 10 moles of ethylene oxide. |
| 14 | "TERGITOL ANIONIC" 7 | Sodium heptadecyl sulphate |
| 15 | "PLURONIC" L64 | A polyoxypropylene block copolymer condensed with ethylene oxide. |
| 16 | "ARYLAN" PWS | An amine salt of dodecylbenzene sulphonic acid. |
| 17 | "GAFAC" PE 510 | Complex mixtures comprising mono- and di-esters of ortho phosphoric acid. |
| 18 | "ETHOMID" HT60 | Condensate of N,N-substituted fatty acid amides with 50 moles of ethylene oxide. |
| 19 | "ARQUAD" 2C75 | Dicoco-dimethylammonium chloride. |
| 20 | "SYNPERONIC" 16 admixed with "SYNPERONIC" B113 (1:1 mixture ratio) | A mostly saturated straight $C_{12}$ - $C_{15}$ alcohol condensed with 16 moles of ethylene oxide - 40% <br> A $C_{11}$ alcohol condensed with 3 moles of ethylene oxide - 40% <br> water - 20% |

The above surface active agents are referred to in McClutcheons Detergent Annual published yearly by the Allured Publishing Company of New Jersey, U.S.A., which lists the manufacturers of the products.

Particularly preferred surface active agents are those numbered 1, 2, 7, 9, 10 and 19 in the above table. Thus a particularly preferred class of non-ionic surface active agents is constituted by the polyether alcohols, especially condensates of alkyl phenols or straight or branched chain fatty alcohols with from 3 to 50 moles of ethylene oxide. In these condensats preferably 1 mole of the alkyl phenol is condensed with from about 3 to about 9 moles of ethylene oxide. The products known by the Trade Marks "Agral" 90, "Lissapol" NX and "Lubrol" APN5 are especially preferred surface active agents of this type.

A further class of non-ionic surface active agents is constituted by esters of polyhydric anhydrides and fatty acids condensed with alkylene oxides. Within this class fatty acid esters of sorbitan condensed with from about 3 to about 80 moles of ethylene oxide are preferred, especially the products known by the Trade Mark "Tween", such as, for example "Tween" 20 and "Tween" 80.

Surface active agents which are relatively non-toxic to plants and mammals are preferred, as are those which can be shown to be readily biodegradable, that is broken down in the environment to known, harmless, chemical substances. Especially preferred are surface active agents appearing on a list approved by the Environmental Protection Agency of the U.S.A. for agricultural usage.

Preferred anionic surface active agents include compounds with hydrophilic groups located towards, or at, the middle of hydrocarbon chains. Salts, for example alkali metal salts, of dialkylsulphonated dicarboxylic acids are especially preferred, a specific example being sodium dioctyl sulphosuccinate.

Preferred cationic surface active agents include alkyl or alkylaryl derivatives of aliphatic or aromatic amines, especially quaternary ammonium halides. Specific examples are didecyldimethyl ammonium bromide and dicocodimethylammonium chloride.

The composition used in the process of this invention, may, in addition to a substance having surface active properties, contain an effective amount of an anti-fungal substance and this may be any known substance having anti-fungal properties. Preferred anti-fungal substances are those haivng activity against the fungal diseases which infect trees, as hereinbefore defined, or which, by virtue of having a different or more potent spectrum of activity, are complementary to the activity displayed by the surface active agent. Suitable fungicides for example, include that known by the common name ethirimol (2-ethylamino-4-methyl-5n-butyl-6-hydroxy pyrimidine - disclosed and claimed in British Pat. No. 1182584) and the pyrimidine sulphamate esters disclosed and claimed in British Patent Application No. 44401/71.

The surface active agent may be used as such but is preferably formulated into a composition by admixture with a carrier, which may be a solid or liquid substance.

The compositions are preferably in the form of liquid preparations to be used as sprays, and are generally solutions, dispersions or emulsions comprising the surface active agent.

The aqueous solutions, dispersions or emulsions may be prepared by dissolving, dispersing or suspending the surface active agent in water, or a mixture of water and an alcohol containing from 1 to 4 carbon atoms. However other liquids, for example organic solvents, may be used, either alone, that is without water being present, or admixed with water.

The compositions to be used as sprays may also be in the form of aerosols wherein the formulation is held in a container under pressure in the presence of a propellant such as fluorotrichloromethane or dichlorodifluoromethane.

By the inclusion of suitable additives, for example for improving the distribution, adhesive power and resistance to rain or treated surfaces, the different compositions can be better adapted for the various uses for which they are intended.

The compositions which are to be used in the form of liquids, for example aqueous solutions dispersions or emulsions, are generally supplied in the form of a concentrate containing a high proportion of the surface active agent, the said concentrate to be diluted with water before use. The concentrates are often required to withstand storage for prolonged periods and after such storage, to be capable of dilution with water in order to form aqueous preparations which remain homogeneous for a sufficient time to enable them to be applied by conventional spray equipment. They may therefore contain adjuvants of known kind to impart such properties to them.

The concentrates may conveniently contain from 10–95% and generally from 25–60% by weight of the active ingredient or active ingredients (if a fungicide is also included). When diluted to form aqueous preparations, such preparations may contain varying amounts of the surface active agent depending upon the purpose for which they are to be used, but an aqueous preparation containing from about 0.5% by volume, or more, of the active ingredient may, for example, be used.

EXAMPLE 1

Apple Powdery Mildew Eradicant Tests

Apple seedlings, 3" to 5" tall, each with 4–6 leaves were inoculated with apple powdery mildew (*Podosphaera leucotricha*) conidia by shaking infected plants over them and allowing the conidia to settle. Five or seven days after inoculation the treatments were applied using a spray gun or air brush. Three or four replicate plants were used for each treatment.

Assessments were made visually of the percentage leaf area infected with apple powdery mildew at intervals after application.

The results are shown for two tests in Table II below. They indicate that the surface active agents alone are somewhat more active against the fungus and cause less phytotoxic damage than a chemical pruning agent containing fatty alcohols.

The active chemicals were, for the purpose of these tests, formulated by mixing or dissolving them in water, or a mixture of water and a lower alcohol containing from 1 to 4 carbon atoms.

TABLE II

| Treatment and Rate in spray on a percentage volume/ volume basis | Test 1 (applied 6.12.72) | | | Test 2 (applied 24.1.73) | | | |
|---|---|---|---|---|---|---|---|
| | % Mildew | Phytotoxicity | | % Mildew | Phytotoxicity | | |
| | 6 days | 2 days | 6 days | 6 days | 1 day | 2 days | 6 days |
| Offshoot T 7.9% | 70 | 3 | 3 | 5 | 3 | 4 | 4–5 |
| Offshoot T 4.8% | 90 | 2 | 3 | 10 | 0 | 1 | 4 |
| Offshoot T 1.6% | 90 | 2 | 2 | | | | |
| Agral 90 5% | 60 | 2 | 3 | 0 | 0 | 2 | 3 |
| Aerosol OT 75 5% | | | | 0 | 0 | 2 | 2 |
| DDAB 5% | | | | 0 | 3 | 5 | 5 |

TABLE II-continued

| Treatment and Rate in spray on a percentage volume/ volume basis | Test 1 (applied 6.12.72) | | | Test 2 (applied 24.1.73) | | | |
|---|---|---|---|---|---|---|---|
| | % Mildew | Phytotoxicity | | % Mildew | Phytotoxicity | | |
| | 6 days | 2 days | 6 days | 6 days | 1 day | 2 days | 6 days |
| Untreated | 100 | 0 | 0 | 100 | 0 | 0 | 0 |

Notes
(1) Rates are percentage product in spray
(2) Days refer to time of assessment - number of days after treatment was applied
(3) In tests 1 and 2, treatments were applied using an Aerograph MP spray gun.
(4) Agral 90 is a non-ionic wetter
(5) Aerosol OT 75 is an anionic wetter
(6) DDAB (didecyldimethylammonium bromide) is a cationic wetter.
(7) Phytotoxicity scale:
0 - no damage
1 - very slight damage
2 - slight damage
3 - moderate damage
4 - severe damage
5 - plant killed
(8) "Offshoot" T is a commercially available chemical pruning agent containing fatty alcohols. (See page 26).

EXAMPLE 2

This Example illustrates the activity of surface active agents when used alone and in conjunction with a fungicide to combat overwintering apple mildew disease (*Podosphaera leucotricha*). Comparison is made with othe, published, chemical treatments for combating this disease. The actual technique usd in the field in the UK is set out below.

Treatments comprising four or five replicate plots were used and the chemical formulations, solutions, emulsions or dispersions of the active chemical or chemicals in water, or water plus a lower alcohol of 1 to 4 carbon atoms, were applied as high volume sprays beyond the point at which the liquid commenced to run-off the trees. This was approximately equivalent to a rate of application of 200 gallons per acre. The trees were Cox's Orange Pippins heavily infected with mildew and they were sprayed during the dormant period after all the leaves had fallen to the ground.

Each "plot" was a 1 to 2 meter long terminal section of a branch which possessed from 40 to 200 buds. At the time of spraying the numbers of visibly healthy buds on the one hand, and of visibly mildew-infected buds on the other, were recorded for each plot.

In the following spring (May 17th – 24th, 1973) the numbers of fruit and vegetative buds visibly infected with mildew (i.e. the number of primary infections) was observed and recorded for each "plot", together with the total number of growing buds (fruit and vegetative) for each plot. The results are presented in the Table III below. In this table the left hand column states the nature of the chemicals used and the percentage amount of the chemical in the actual spray applied (N.B. on a volume basis for surface active agents and on a weight basis for fungicidal substances). In subsequent columns the figures given are mean numbers of mildew-infected buds per treatment expressed as a percentage of the number of mildewed buds in untreated plots as observed and recorded between 17th and 24th May 1973.

There was no obvious damage caused by the treatments and they had no effect upon the total number of growing buds. Some of the treatments caused slight delay in bud-burst; this is not considered a disadvantage and could even be an advantage in some situations by avoiding a risk of frost damage.

TABLE III

| Chemical Treatment (Water containing 5%, by volume, of the surface active agent) | Season and Date of Spray Application | | | | |
|---|---|---|---|---|---|
| | Single Autumn or Winter 1972 Application | | | Single Spring 1973 Application | |
| | 29 Nov | 13 Dec | 26 Jan | 15 Mar | 20 Mar |
| Agral 90 (5% by volume) | 64 | 15 | 0 | 25 | 0 |
| Aerosol OT 75 (5% by volume) | — | 0.3 | 0 | — | — |
| Tween 20 (5% by volume) | — | 35 | — | — | — |
| Agral 90 + Ethirimol (5% by volume) (1% by weight) | — | 0 | 0 | — | — |
| Aerosol OT 75 + Ethirimol (5% by volume) (1% by weight) | — | 0.6 | — | — | — |
| Tween 20 + Ethirimol (5% by volume) (1% by weight) | — | 0.9 | — | — | — |
| DDAB + Ethirimol (5% by volume) (0.1% by weight) | — | — | 0 | — | — |
| DDAB + Ethirimol (5% by volume) 1.0% by weight) | — | — | 0 | — | — |
| DDAB + Ethirimol (3% by volume) (1% by weight) | — | — | 0 | — | — |
| "Offshoot" T (7.9% by volume) | 74 | 70 | 20 | 68 | 50 |
| "Offshoot" O (11.1% by volume) | — | — | 31 | — | — |
| Untreated* | 100 | 100 | 100 | 100 | 100 |

*The actual percentage amount of mildew on the untreated

TABLE III-continued

| Chemical Treatment (Water containing 5%, by volume, of the surface active agent) | Season and Date of Spray Application | | | | |
|---|---|---|---|---|---|
| | Single Autumn or Winter 1972 Application | | | Single Spring 1973 Application | |
| | 29 Nov | 13 Dec | 26 Jan | 15 Mar | 20 Mar |
| trees was | 46.3 | 33.9 | 5.7 | 46.3 | 14.8 |

N.B.
The above valued are not directly comparable horizontally since different sites were sprayed at different dates.

"Offshoot" O comprises 45% of methyl esters of $C_6$ to $C_{12}$ fatty acids and 55% of inert ingredients. The make-up of the esters is believed to be as follows: methyl hexanoate 4%; methyl octanoate 56%; methyl decanoate 38%; methyl dodecanoate 2%. The inert ingredients are believed to comprise polyoxyethylene (20) Sorbitan monododecanoate ("Tween 20") 45% and water 10%.

"Offshoot" T comprises 63% of $C_6$ to $C_{12}$ fatty alcohols and 37% of inert ingredients. The makeup of the fatty alcohols is believed to be n-hexyl alcohol 0.5%; n-octyl alcohol 42%; n-decyl alcohol 56%; n-dodecyl alcohol 1.5%. The inert ingredients are believed to comprise a "Tween" wetting agent.

EXAMPLE 3

In mid-autumn selected branches of apple (variety Jonathan) trees were sprayed with aqueous solutions of a number of surace active agents. There were six trees, and branches on each tree were subjected to each spray treatment. The experiments were conducted at two sites (site A and site B) and an assessment was made in the late spring of the numbers of healthy buds on the one hand, and the number carrying the powdery mildew disease Podosphaera leucotricha on the other.

The results are given in Table IV below, in the first column of which is presented the commercial name of the surface active agent used (reference should be made to Table I hereinbefore for the chemical nature of the surface active agent). The second column states concentration of the surface active agent used and the third and fourth columns give the percentage number of infected buds observed at spring assessment.

TABLE IV

| Surface Active Agent TRADE MARK | Concentration in percentage volume | Percentage Number of Diseased buds | |
|---|---|---|---|
| | | Site A | Site B |
| AGRAL 90 | 5 | 22.00 | 6.67 |
| LUBROL APN 5 | 5 | 16.33 | 2.93 |
| LUBROL L | 5 | 39.67 | 11.18 |
| RENEX 30 | 5 | 31.33 | 5.83 |
| AEROSOL OT75 | 5 | 5.67 | 1.14 |
| ETHOMID HT60 | 5 | 45.67 | 22.01 |
| ARQUAD 2C75 | 5 | 20.00 | 1.07 |
| LUBROL W | 5 | 44.33 | 12.43 |
| Untreated Control | | 53.00 ⎫ 54.00 | 23.25 ⎫ 22.07 |
| " | | 55.00 ⎭ | 20.89 ⎭ |

We claim:
1. A process for combating overwintering powdery mildew in trees comprising spraying said trees while in a dormant phase with an antifungally effective amount of an aqueous composition consisting essentially of water and at least 0.5% by volume of an active ingredient which is a surface active compound, said surface active compound being a polyether alcohol which is a condensate of (a) 1 mole of nonyl phenol, octyl phenol, octyl cresol, tridecyl alcohol, dodecyl alcohol, a mixture of $C_{16}$ to $C_{18}$ alcohols or a mixture of $C_{12}$ to $C_{15}$ alcohols, with (b) 3–50 moles of ethylene oxide.

2. A process according to claim 1 wherein the polyether alcohol is a condensate of monyl phenol with from 3 to 9 moles of ethylene oxide.

3. A process according to claim 1 wherein the trees are apple trees which are sprayed against Podosphaera leucotricha.

4. A process according to claim 1 wherein the composition additionally contains a minor amount of an alcohol containing from 1 to 4 carbon atoms.

* * * * *

UNITED STATES PATENT OFFICE
CERTIFICATE OF CORRECTION

Patent No. 3,984,570     Dated October 5, 1976

Inventor(s) Keith Joseph BENT and John Angus William TURNER

It is certified that error appears in the above-identified patent and that said Letters Patent are hereby corrected as shown below:

Claim 2, line 2, "monyl" should be --nonyl--

Signed and Sealed this

Fourth Day of January 1977

[SEAL]

*Attest:*

RUTH C. MASON
*Attesting Officer*

C. MARSHALL DANN
*Commissioner of Patents and Trademarks*